(12) United States Patent
Musa

(10) Patent No.: US 6,300,456 B1
(45) Date of Patent: Oct. 9, 2001

(54) COMPOUNDS WITH ELECTRON DONOR AND ELECTRON ACCEPTOR FUNCTIONALITY

(75) Inventor: Osama M. Musa, Hillsborough, NJ (US)

(73) Assignee: National Starch and Chemical Investment Holding Corporation, Wilmington, DE (US)

( * ) Notice: Subject to any disclaimer, the term of this patent is extended or adjusted under 35 U.S.C. 154(b) by 0 days.

(21) Appl. No.: 09/573,838

(22) Filed: May 18, 2000

(51) Int. Cl.$^7$ .................................................. C08G 18/04
(52) U.S. Cl. .............................. 528/44; 528/32; 528/45; 528/59; 528/272; 526/335; 568/606; 568/27; 568/28; 568/38; 568/308; 568/579; 558/254; 560/330; 564/17; 564/32; 564/47
(58) Field of Search ................................ 528/32, 44, 45, 528/59, 272; 526/335; 568/606, 27, 28, 308, 579; 558/254; 560/330; 564/17, 32, 47

(56) References Cited

U.S. PATENT DOCUMENTS

| | | | |
|---|---|---|---|
| 4,486,582 | 12/1984 | Heffner, Jr. | 526/301 |
| 4,543,397 | 9/1985 | Woods et al. | 525/455 |
| 4,640,849 | 2/1987 | Woods et al. | 427/54.1 |
| 4,732,956 | 3/1988 | Woods et al. | 526/260 |
| 4,749,807 | 6/1988 | Lapin et al. | 560/91 |
| 4,751,273 | 6/1988 | Lapin et al. | 525/455 |
| 4,775,732 | 10/1988 | Lapin et al. | 528/49 |
| 5,019,629 | 5/1991 | Woods et al. | 525/312 |
| 5,084,490 | 1/1992 | McArdle et al. | 522/181 |
| 5,183,946 | 2/1993 | Liu et al. | 568/670 |
| 5,334,456 | 8/1994 | Noren et al. | 428/431 |
| 5,491,178 | 2/1996 | Swedo et al. | 522/74 |
| 5,514,727 | 5/1996 | Green et al. | 522/15 |
| 5,516,455 | 5/1996 | Jacobine et al. | 252/299.01 |
| 5,539,014 | 7/1996 | Swedo et al. | 522/91 |
| 5,633,411 | 5/1997 | Woods et al. | 568/654 |
| 5,708,129 | 1/1998 | Nguyen et al. | 528/362 |
| 5,789,757 | 8/1998 | Husson, Jr. et al. | 252/183.11 |
| 6,034,194 | 3/2000 | Dershem et al. | 526/262 |
| 6,034,195 | 3/2000 | Dershem et al. | 526/262 |

OTHER PUBLICATIONS

"Co–Polymerization of Maleimides and Vinyl Ethers: A Structural Study" by P. Kohli, A. B. Scranton, and G. J. Blanchard; *Macromolecules 1998*, 31, 5681–5689.

*Primary Examiner*—Robert Dawson
*Assistant Examiner*—Kuo-Liang Peng
(74) *Attorney, Agent, or Firm*—Jane E. Gennaro

(57) ABSTRACT

Compounds containing both electron donor and electron acceptor functionality are suitable for use in adhesives. The electron donor group is a carbon to carbon double bond attached to an aromatic ring and conjugated with the unsaturation in the ring. The electron acceptor group is a maleimide, acrylate, fumarate or maleate.

4 Claims, No Drawings

COMPOUNDS WITH ELECTRON DONOR AND ELECTRON ACCEPTOR FUNCTIONALITY

FIELD OF THE INVENTION

This invention relates to electron donor/acceptor compounds and to curable adhesive compositions comprising those electron donor/acceptor compounds.

BACKGROUND OF THE INVENTION

Adhesive compositions, particularly conductive adhesives, are used for a variety of purposes in the fabrication and assembly of semiconductor packages and microelectronic devices. The more prominent uses are the bonding of integrated circuit chips to lead frames or other substrates, and the bonding of circuit packages or assemblies to printed wire boards.

There exist electron acceptor/donor adhesives, using vinyl ethers as donors, for use in low modulus adhesives, particularly in fast-cure adhesives for die attach applications. However, the number of suitable vinyl ethers as donors is limited due to high volatility and difficulty in preparation. Thus, there is a need for the development of new electron donor/acceptor compounds for use in adhesives applications.

SUMMARY OF THE INVENTION

This invention relates to compounds containing both an electron donor group and an electron acceptor group (electron donor/acceptor compound). The electron donor group is a carbon to carbon double bond attached to an aromatic ring and conjugated with the unsaturation in the ring. The electron acceptor group is a maleate, fumurate, maleimide, or acrylate. This invention is also an adhesive composition comprising one or more of the inventive electron donor/acceptor compounds, a curing agent, and optionally, one or more fillers.

DETAILED DESCRIPTION OF THE INVENTION

The electron donor/acceptor compounds of this invention will have one of the structures depicted here:

Structure I:

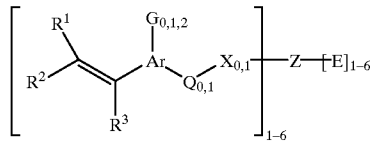

Structure II:

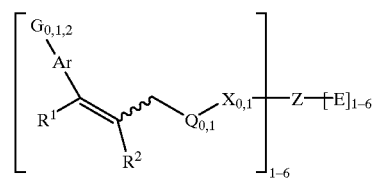

in which
  Ar is an aromatic or heteroaromatic ring or fused ring having 3 to 10 carbon atoms within the ring structure, in which the heteroatom is N, O or S;
  $R^1$, $R^2$ and $R^3$ are independently hydrogen, a branched, cyclic or linear alkyl group having 1 to 12 carbon atoms, or Ar as described above; preferably, $R^1$ $R^2$ and $R^3$ are hydrogen or a methyl or ethyl group;
  G is $-OR^4$, $-SR^4$, $-N(R^1)(R^2)$, Ar as described above, or an alkyl group having 1 to 12 carbon atoms, in which $R^1$ and $R^2$ are as described above, and $R^4$ is Ar as described above or an alkyl group having 1 to 12 carbon atoms, preferably 1 to 4 carbon atoms;
  Q is an alkyl group having 1 to 12 carbon atoms;
  X is:

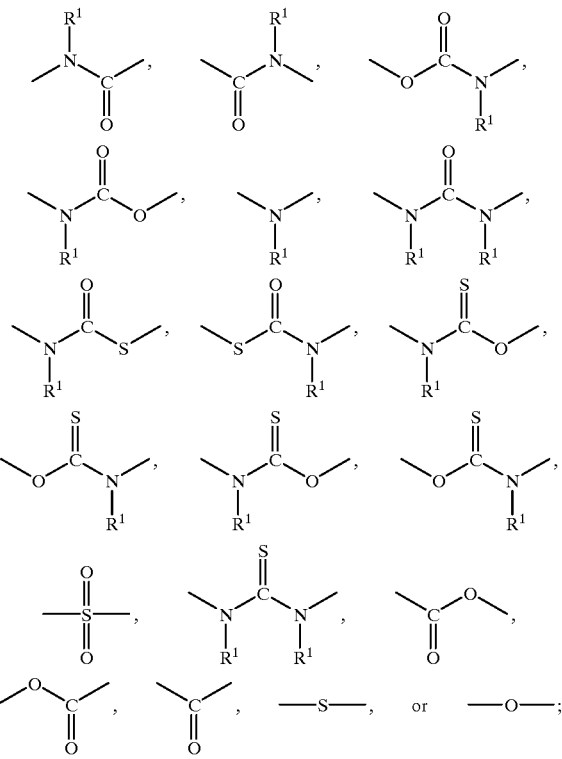

Z is an alkyl group, a siloxane, a polysiloxane, a $C_1$ to $C_4$ alkoxy-terminated siloxane or polysiloxane, a polyether, a polyester, a polyurethane, a poly(butadiene) or an aromatic, polyaromatic, or heteroaromatic group; and
  E is

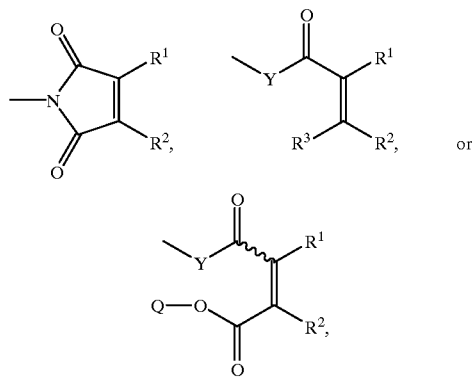

in which Y is O or $N(R^1)$ and $R^1$, $R^2$, and $R^3$ and Q are as described above.

The electron donor group is a carbon-carbon double bond that is attached directly to an aromatic ring and conjugated with the unsaturation in the aromatic ring. The aromatic ring can be any molecular moiety that meets the classical definition of an aromatic compound, that is it contains cyclic clouds of delocalized π electrons above and below the plane of the molecule and the π clouds have a total of (4n+2) electrons.

The aromatic ring may also contain electron donating substituents, which will increase the electron density on the carbon to carbon double bond, leading to higher reactivity. The reactivity of the electron donor group will also be affected by steric interaction. An increase in the number of alkyl substituents on the carbon to carbon double bond will decrease the reactivity. Preferably, all substituents on the carbon to carbon double bond will be hydrogen, or will be hydrogen with a methyl group as the only other substituent.

Starting materials for Z group moieties are commercially available from a number of sources; for example, aromatic and polyaromatic materials may be obtained from BASF or Bayer; siloxanes and polysiloxanes from Gelest; polyethers from BASF; polyesters from Uniqema or Bayer; poly(butadiene)s from Elf-Atochem; polyurethanes from Bayer or BASF; and the branched or linear alkanes from Uniqema.

The Z groups may contain cyclic moieties or heteroatoms, and may contain pendant hydroxyl or thiol groups depending on the synthetic route for making the electron donor compound; for example, if one of the starting compounds contains a hydroxyl or thiol functionality that is reacted with an epoxy functionality, the Z group will contain a pendant hydroxyl or thiol group.

The exact composition or molecular weight of Z is not critical to the invention and can range widely depending on the requirements of the end use for the electron donor compound. For example, Z can be a methylene group or a high molecular weight polymeric entity. The composition of Z can be chosen to give specific material properties in a final formulation, such as, rheological properties, hydrophilic or hydrophobic properties, toughness, strength, or flexibility. For example, a low level of crosslinking and free rotation about polymeric bonds will impart flexibility to a compound, and the presence of siloxane moieties will impart hydrophobicity and flexibility. The molecular weight and chain length will affect viscosity, the higher the molecular weight and the longer the chain length, the higher the viscosity.

The electron acceptor starting compounds can be fumarates and maleates, acrylates and maleimides. Suitable acrylates are numerous and are commercially available, for example, from Sartomer. Suitable maleimides are easily prepared, for example, according to procedures described in U.S. Pat. Nos. 6,034,194 and 6,034,195 to Dershem. In general, the carboxyl group in the acrylate, maleate and fumarate compounds will be the reactive functionality for linking the electron acceptor to a co-reactive functionality on the Z group. The maleimides will contain a separate functionality, as shown in the examples, for reacting with a co-reactive functionality on the Z group.

Suitable reaction routes can be designed by determining on a specific addition or condensation reaction, then choosing functionalities for the starting electron-donor compound and the starting electron-acceptor compound to participate in that reaction. Although one skilled in the art can devise suitable variations in reactions by choice and location of functionality (whether on the starting electron-donor or starting electron-acceptor compound), it will be understood that the choices may be limited in practice by the commercial availability of starting materials or ease of synthesis routes.

Representative synthetic routes include:
1. the reaction of isocyanate functionality with (i) hydroxyl; or (ii) amine; or (iii) thiol functionality to create a carbamate linkage, urea or thiocarbamate respectively;
2. the substitution of a halogen with (i) hydroxyl; or (ii) amine; or (iii) thiol functionality to create an ether linkage, amine or thio-ether respectively;
3. the reaction of an epoxy functionality with (i) hydroxyl; or (ii) amine; or (iii) thiol functionality to create an ether linkage, amine or thio-ether respectively.

The electron donor/acceptor compounds can be formulated into an adhesive, coating, potting or encapsulant composition. In addition to the electron donor/acceptor compound, the formulations will contain one or more curing agents and may contain a conductive or nonconductive filler.

Exemplary curing agents are thermal initiators and photoinitiators and will be present in an amount of 0.1% to 10%, preferably 0.1% to 3.0%, by weight of the electron donor compound. Preferred thermal initiators include peroxides, such as butyl peroctoates and dicumyl peroxide, and azo compounds, such as 2,2'-azobis(2-methyl-propanenitrile) and 2,2'-azobis(2-methyl-butanenitrile). A preferred series of photoinitiators is one sold under the trademark Irgacure by Ciba Specialty Chemicals. In some formulations, both thermal initiation and photoinitiation may be desirable; for example, the curing process can be started by irradiation, and in a later processing step curing can be completed by the application of heat to accomplish the thermal cure.

In general, these compositions will cure within a temperature range of 70° C. to 250° C., and curing will be effected within a range of ten seconds to three hours. The time and temperature curing profile of each formulation will vary with the specific electron donor compound and the other components of the formulation, but the parameters of a curing profile can be determined by one skilled in the art knowing the teachings of this specification.

Suitable conductive fillers are carbon black, graphite, gold, silver, copper, platinum, palladium, nickel, aluminum, silicon carbide, boron nitride, diamond, and alumina. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. When present, fillers will be in amounts of 20% to 90% by weight of the formulation.

Suitable adhesion promoters or coupling agents are silanes, silicate esters, metal acrylates or methacrylates, titanates, and compounds containing a chelating ligand, such as phosphine, mercaptan, and acetoacetate. When present, coupling agents will be in amounts up to 10% by weight, and preferably in amounts of 0.1% to 3.0% percent by weight of the electron donor compounds.

In addition, the formulations may contain compounds that lend additional flexibility and toughness to the resultant cured material. Such compounds may be any thermoset or thermoplastic material having a Tg of 150° C. or less, and typically will be a polymeric material, such as, a polyacrylate, poly(butadiene), polyTHF (polymerized tetrahydrofuran), carboxy-terminated butyronitrile rubber and polypropylene glycol. When present, these compounds may be in an amount up to about 15% by weight of the electron donor compound.

EXAMPLES

The following examples show representative electron donor/acceptor compounds and reactions for their prepara-

Example 1

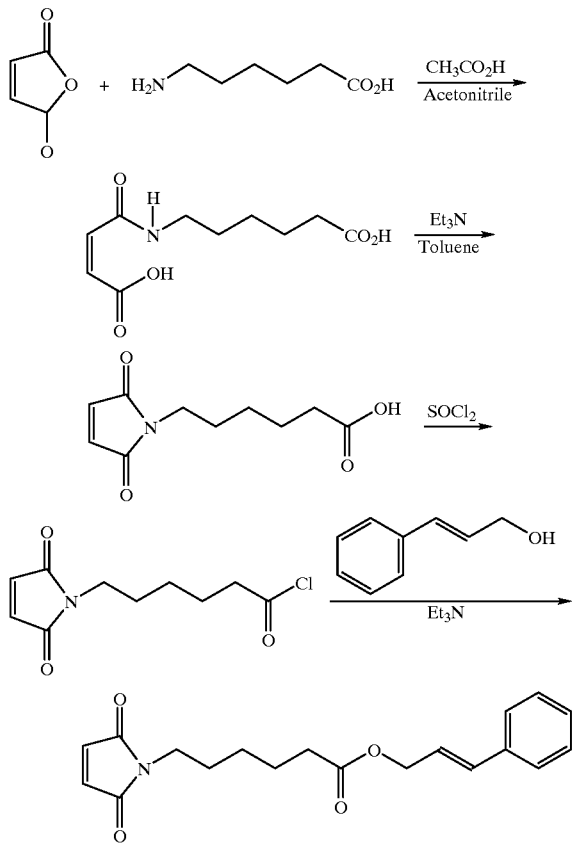

A solution of one molar equivalent maleic anhydride in acetonitrile is added to one molar equivalent of 6-aminocaproic acid in acetic acid. The mixture is allowed to react for three hours at room temperature until white crystals of the amic acid adduct precipitate from the solution. The white crystals are filtered off, washed with cold acetonitrile, and dried.

The amic acid is mixed with two molar equivalents of triethylamine in toluene. The mixture is heated to 130° C. for two hours and until water is distilled off. The organic solvent is evaporated and 2M HCl is added to reach pH 2. The mixture is extracted with ethyl acetate and dried over $MgSO_4$. The solvent is evaporated to give the 6-maleimidocaproic acid.

The 6-maleimidocaproic acid is reacted with excess thionyl chloride at 50° C. for three hours, and then the excess thionyl chloride is distilled off to leave 6-maleimidocaproic chloride.

One molar equivalent each of cinnamyl alcohol and triethylamine are mixed in dry methylene chloride at 0° C., to which is added 6-maleimidocaproic chloride dissolved in dry methylene chloride. This mixture is allowed to react for four hours. The solvent is evaporated and the crude product is purified by column chromatography using a gradient of hexane/ethyl acetate.

Example 2

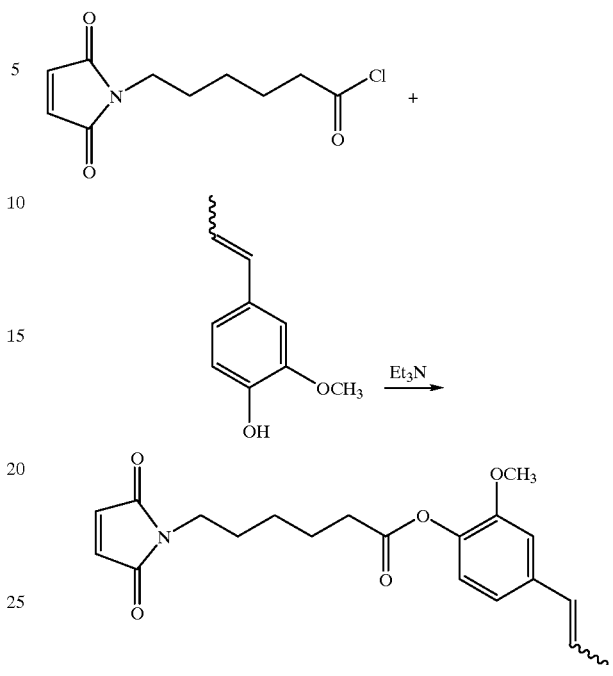

One molar equivalent of isoeugenol and one molar equivalent of triethylamine are mixed in dry methylene chloride at 0° C. to which is added one molar equivalent of 6-maleimidocaproic chloride dissolved in dry methylene chloride. This mixture is allowed to react for four hours. The solvent is evaporated and the crude product is purified by column chromatography using a gradient of hexane/ethyl acetate.

Example 3

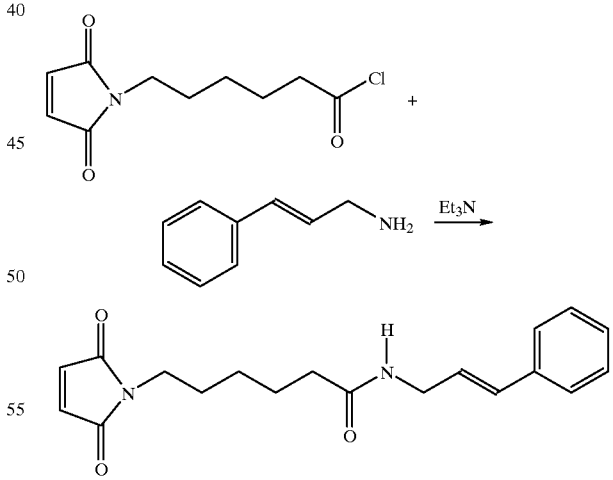

One molar equivalent of cinnamyl amine and one molar equivalent of triethylamine are mixed in dry methylene chloride at 0° C. to which is added one molar equivalent of 6-maleimidocaproic chloride dissolved in dry methylene chloride. The mixture is allowed to react for four hours. The solvent is evaporated and the crude product is purified by column chromatography using a gradient of hexane/ethyl acetate.

Example 4

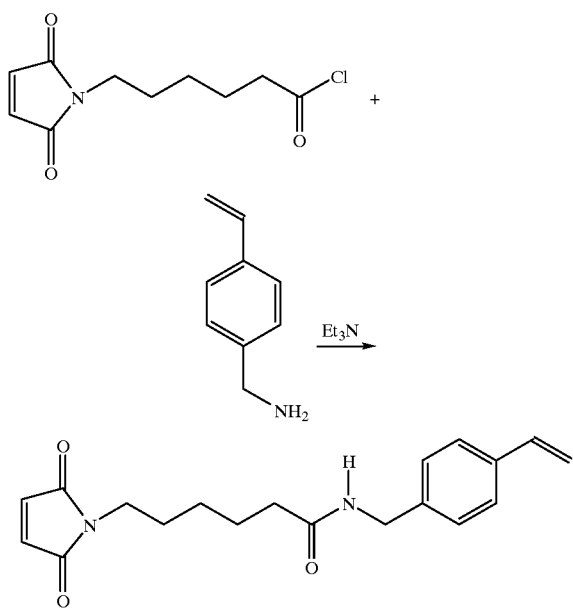

One molar equivalent of 4-vinyl benzyl amine and one molar equivalent of triethylamine are mixed in dry methylene chloride at 0° C., to which is added one molar equivalent of 6-maleimidocaproic chloride dissolved in dry methylene chloride. The mixture is allowed to react for four hours. The solvent is evaporated and the crude product is purified by column chromatography using a gradient of hexane/ethyl acetate.

Example 5

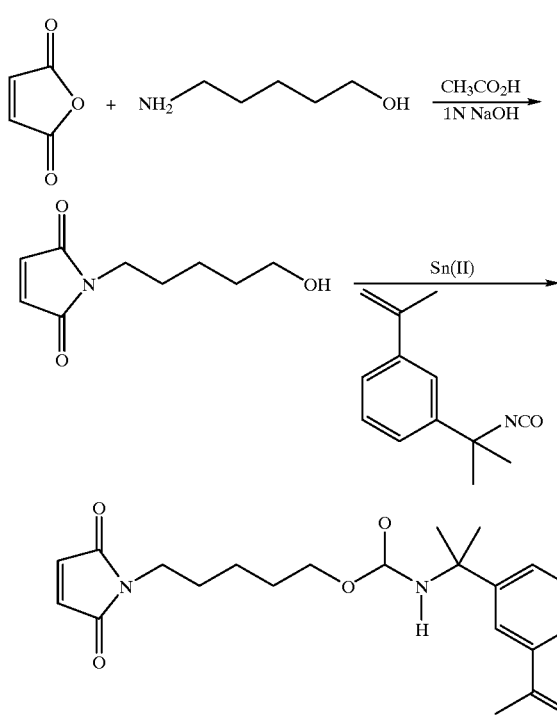

One molar equivalent of maleic an hydride and one molar equivalent of 5-amino pentanol are dissolved in anhydrous acetic acid and the solution is heated to reflux for eight hours. The acetic acid is distilled off and the residue dissolved in diethyl ether. The diethyl ether solution is washed once with 1 N NaOH, twice with water, and then dried over $MgSO_4$. The diethyl ether is evaporated, and the residue is crystallized from isopropyl ether to produce N-(5-hydroxypentyl)maleimide.

One molar equivalent of 3-isopropenyl-$\alpha,\alpha$-dimethylbenzyl isocyanate (m-TMI) is solvated in toluene in a three-necked flask equipped with a mechanical stirrer, addition funnel and nitrogen inlet/outlet. The reaction is placed under nitrogen, and 0.01 molar molar equivalent dibutyltin dilaurate (catalyst) is added with stirring as the solution is heated to 90° C. The addition funnel is charged with one molar equivalent of N-(5-hydroxypentyl) maleimide dissolved in toluene. This solution is added to the isocyanate solution over ten minutes, and the resulting mixture heated for an additional three hours at 90° C. The reaction is allowed to cool to room temperature, and then the mixture is washed with distilled water three times. The organic layer is isolated and dried over $MgSO_4$, filtered, and the solvent removed in vacuo to give the product.

Example 6

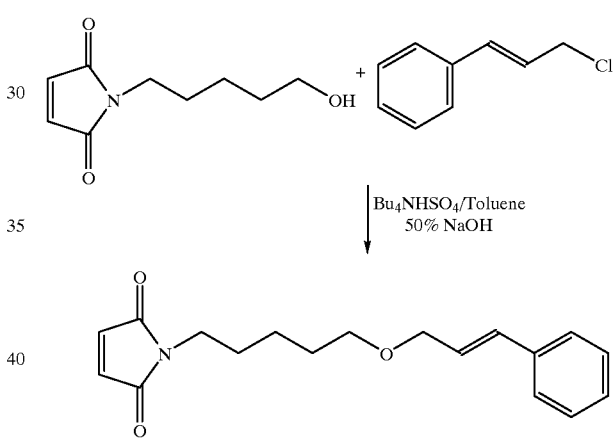

One molar equivalent of N-(5-hydroxypentyl)maleimide, excess of 50% NaOH, 0.43 molar molar equivalent of tetrabutyl ammonium hydrogen sulfate, and one molar equivalent of cinnamyl chloride in toluene are stirred for five hours at 53° C., then 15 hours at 75° C. The reaction is allowed to cool to room temperature and the organic layer extracted and washed with brine three times. The isolated organic layer is then dried over $MgSO_4$, filtered, and the solvent removed in vacuo to give the cinnamyl chloride/pentanol maleimide adduct.

Example 7

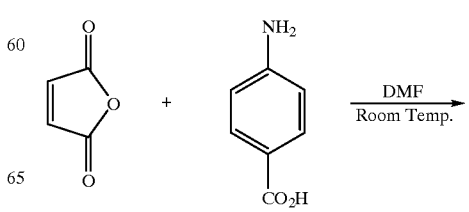

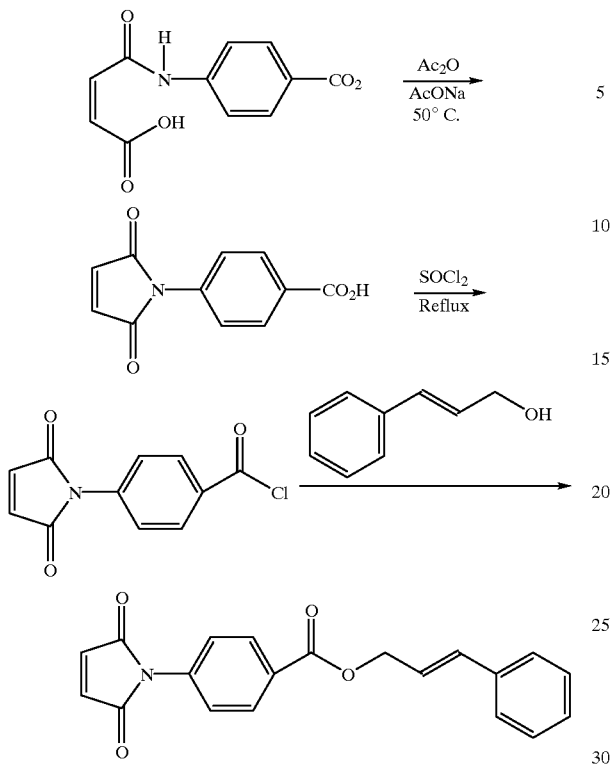

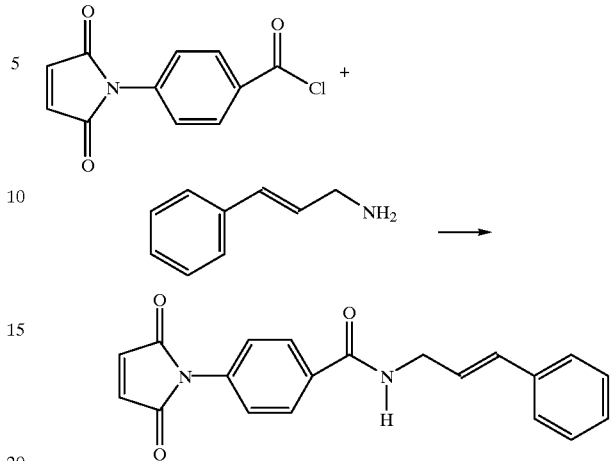

Example 8

One molar equivalent of cinnamyl amine and one molar equivalent of triethylamine are mixed in dry methylene chloride at 0° C., to which is added one molar equivalent of N-(4-(chlorocarbonyl)phenyl)maleimide dissolved in dry methylene chloride. The mixture is allowed to react for four hours. The solvent is evaporated and the crude product is purified by column chromatography using a gradient of hexane/ethyl acetate.

One molar equivalent of maleic anhydride and p-amino benzoic acid are dissolved in N,N-dimethylformamide (DMF), and the mixture stirred at room temperature for five hours under nitrogen atmosphere. The resulting solution is poured into a sufficient water to precipitate crude N-(4-carboxyphenyl)maleamic acid. This is filtered, dried, and recrystallized three times from water to obtain pure N-(4-carboxyphenyl)maleamic acid.

A mixture of one molar equivalent N-(4-carboxyphenyl) maleamic acid, acetic anhydride, and sodium acetate is stirred at 60° C. for two hours. The reaction mixture is poured into a sufficient amount of water to precipitate crude N-(4-carboxyphenyl)maleimide. This is filtered, dried, and recrystallized three times from water to obtain pure N-(4-carboxyphenyl)maleimide.

A mixture of one molar equivalent of N-(4-carboxyphenyl)maleimide is reacted with excess thionyl chloride at 50° C. for three hours. The excess thionyl chloride is distilled off, and the residual product recrystallized from benzene to obtain pure N-(4-(chlorocarbonyl) phenyl)maleimide.

One molar equivalent cinnamyl alcohol and one molar equivalent triethylamine are mixed in dry methylene chloride at 0° C. to which is added N-(4-(chlorocarbonyl)phenyl) maleimide dissolved in dry methylene chloride. The mixture is allowed to react for four hours. The solvent is evaporated and the crude product is purified by column chromatography using a gradient of hexane/ethyl acetate.

Example 9

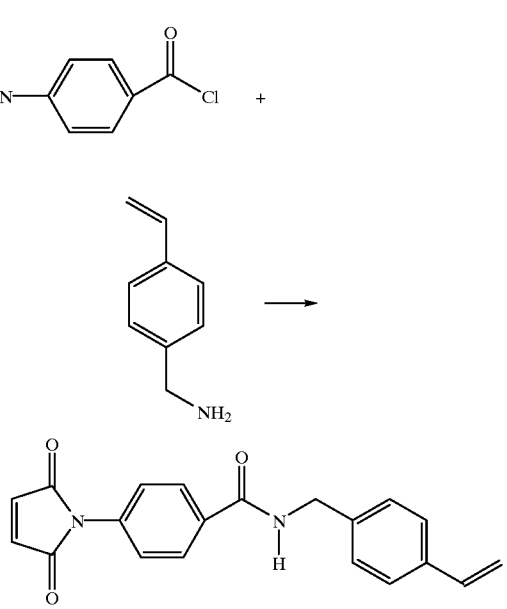

One molar equivalent of 4-vinyl benzyl amine and one molar equivalent of triethylamine are mixed in dry methylene chloride at 0° C., to which is added one molar equivalent of N-(4-(chlorocarbonyl)phenyl)maleimide dissolved in dry methylene chloride. The mixture is allowed to react for four hours. The solvent is evaporated and the crude product is purified by column chromatography using a gradient of hexane/ethyl acetate.

Example 10

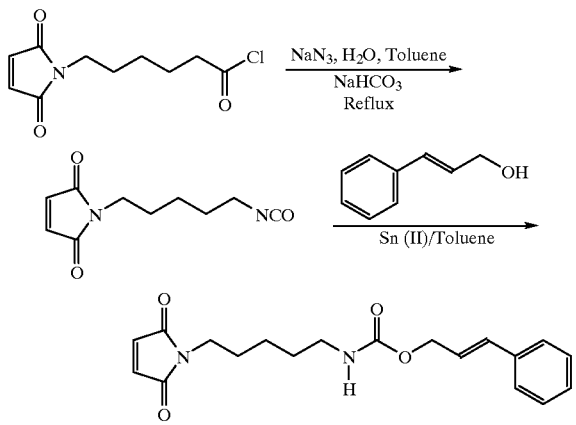

With vigorous stirring, a mixture of one molar equivalent sodium azide in water and toluene and a catalytic amount of benzyltriethyl-ammonium chloride is cooled to 10° C. in a round-bottom flask. One molar equivalent of 6-maleimidocaproic chloride is added dropwise to this solution over approximately 40 minutes. The solution is stirred for one hour at 15° C. and then for one hour at 20° C. The organic phase is separated off and washed with 2N aqueous sodium bicarbonate solution and with water. The organic phase is dried with $MgSO_4$ and filtered. The filtrate is introduced into a round-bottom flask and heated slowly to reflux. Reflux is maintained until the evolution of nitrogen has ceased. The solution is heated under reflux for a further 30 minutes and, after cooling, is concentrated using a rotary evaporator. The residue is distilled under a high vacuum to produce the maleimide with isocyanate functionality.

One molar equivalent of maleimide with isocyanate functionality is solvated in toluene in a three-necked flask equipped with a mechanical stirrer, addition funnel and nitrogen inlet/outlet. The reaction is placed under nitrogen, and 0.01 molar molar equivalent dibutyltin dilaurate (catalyst) is added with stirring as the solution is heated to 70° C. The addition funnel is charged with one molar equivalent of cinnamyl alcohol dissolved in toluene. This solution is then added to the isocyanate solution over ten minutes, and the resulting mixture heated for an additional three hours at 70° C. After the reaction is allowed to cool to room temperature, the mixture is washed with distilled water three times. The isolated organic layer is then dried over $MgSO_4$, filtered and the solvent removed in vacuo to give the product.

Example 11

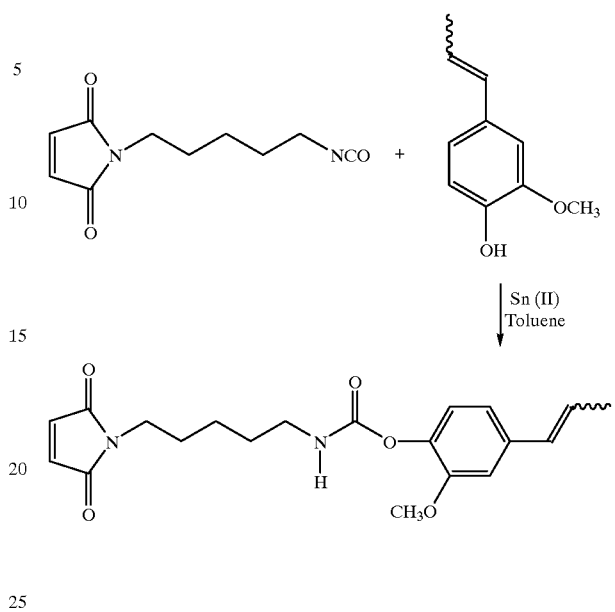

One molar equivalent of maleimide with isocyanate functionality is solvated in toluene in a three-necked flask equipped with a mechanical stirrer, addition funnel and nitrogen inlet/outlet. The reaction is placed under nitrogen, and 0.01 molar molar equivalent dibutyltin dilaurate (catalyst) is added with stirring as the solution is heated to 70° C. The addition funnel is charged with one molar equivalent of isoeugenol dissolved in toluene. This solution is then added to the isocyanate solution over ten minutes, and the resulting mixture heated for three hours at 70° C. After the reaction is allowed to cool to room temperature, the mixture is washed with distilled water three times. The isolated organic layer is then dried over $MgSO_4$, filtered, and the solvent removed in vacuo to give the product.

Example 12

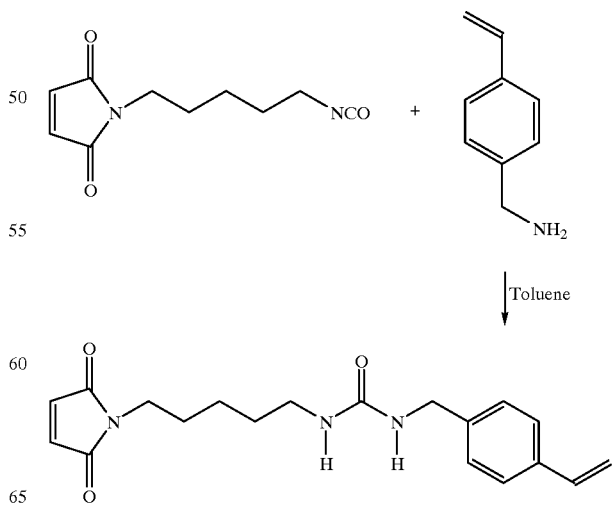

One molar equivalent of maleimide with isocyanate functionality is solvated in toluene in a three-necked flask equipped with a mechanical stirrer, addition funnel and nitrogen inlet/outlet. The addition funnel is charged with one molar equivalent of 4-vinyl benzyl amine dissolved in toluene. This solution is then added to the isocyanate solution over ten minutes, and the resulting mixture heated for an additional three hours at 70° C. After the reaction is allowed to cool to room temperature, the mixture is washed with distilled water three times. The isolated organic layer is dried over MgSO$_4$, filtered, and the solvent removed in vacuo to give the product.

Example 13

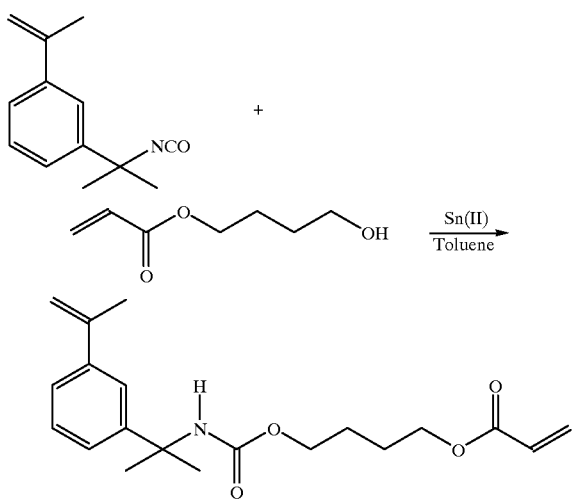

One molar equivalent of 3-isopropenyl-α,α-dimethylbenzyl isocyanate (m-TMI) is solvated in toluene in a three-necked flask equipped with a mechanical stirrer, addition funnel and nitrogen inlet/outlet. The reaction is placed under nitrogen, and 0.01 molar molar equivalent of dibutyltin dilaurate (catalyst) is added with stirring as the solution is heated to 70° C. The addition funnel is charged with one molar equivalent of butanediol monoacrylate dissolved in toluene. This solution is added to the isocyanate solution over ten minutes, and the resulting mixture heated for an additional three hours at 70° C. After the reaction is allowed to cool to room temperature, the mixture is washed with distilled water three times. The isolated organic layer is then dried over MgSO$_4$, filtered, and the solvent removed in vacuo to give product.

Example 14

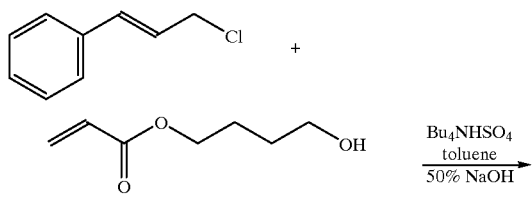

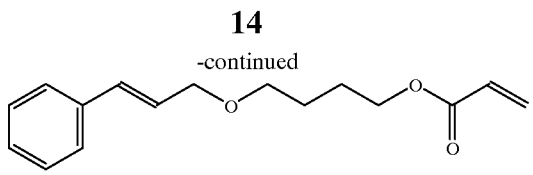

One molar equivalent of butanediol monoacrylate, excess of 50% NaOH, 0.43 molar molar equivalent of tetrabutyl ammonium hydrogen sulfate, and one molar equivalent of cinnamyl chloride in toluene are stirred for five hours at 53° C., then for 15 hours at 75° C. The reaction is allowed to cool to room temperature, after which organic layer is extracted and washed with brine three times. The isolated organic layer is dried over MgSO$_4$, filtered, and the solvent removed in vacuo to give the product.

Example 15

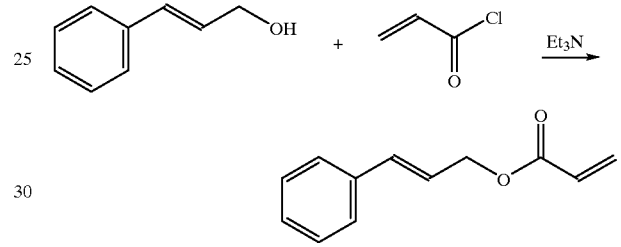

One molar equivalent each of cinnamyl alcohol and triethylamine are mixed in dry methylene chloride at 0° C. to which is added one molar equivalent of acryloyl chloride dissolved in dry methylene chloride. The mixture is allowed to react for four hours. The solvent is evaporated and the crude product is purified by column chromatography using a gradient of hexane/ethyl acetate.

Example 16

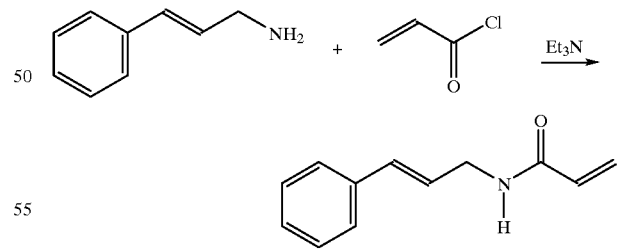

One molar equivalent each of cinnamyl amine and triethylamine are mixed in dry methylene chloride at 0° C., to which is added one molar equivalent of acryloyl chloride dissolved in dry methylene chloride. The mixture is allowed to react for four hours. The solvent is evaporated and the crude product is purified by column chromatography using a gradient of hexane/ethyl acetate.

Example 17

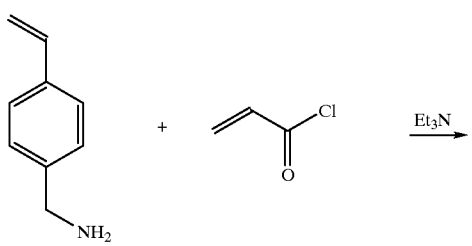

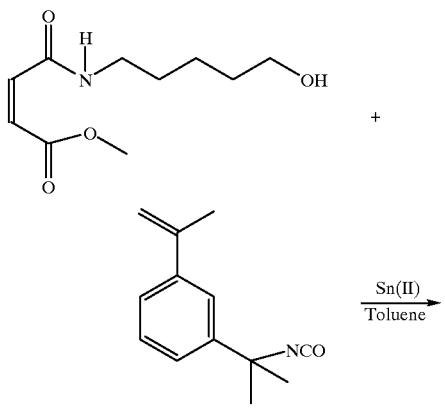

One molar equivalent each of 4-vinyl benzyl amine and triethylamine are mixed in dry methylene chloride at 0° C., to which is added one molar equivalent of acryloyl chloride dissolved in dry methylene chloride. The mixture is allowed to react for four hours. The solvent is evaporated and the crude product is purified by column chromatography using a gradient of hexane/ethyl acetate.

Example 18

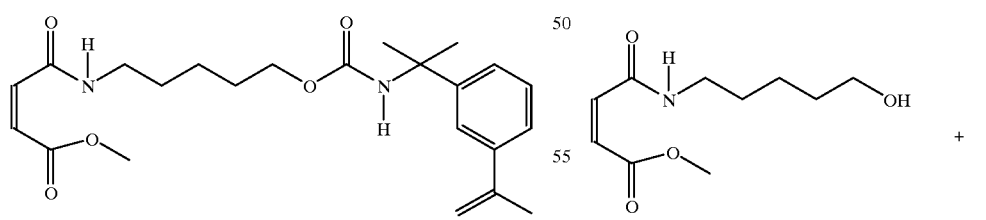

One molar equivalent of 3-isopropenyl-α,α-dimethylbenzyl isocyanate (m-TMI) is solvated in toluene in a three-necked flask equipped with a mechanical stirrer, addition funnel and nitrogen inlet/outlet. The reaction is placed under nitrogen, and 0.01 molar equivalent of dibutyltin dilaurate (catalyst) is added with stirring as the solution is heated to 70° C. A solution of one molar equivalent of hydroxyl amic ester dissolved in toluene is added to the isocyanate solution over ten minutes, and the resulting mixture heated for an additional three hours at 70° C. After the reaction is allowed to cool to room temperature, the mixture is washed with distilled water three times. The isolated organic layer is then dried over MgSO$_4$, filtered and the solvent removed in vacuo to give the product.

Example 19

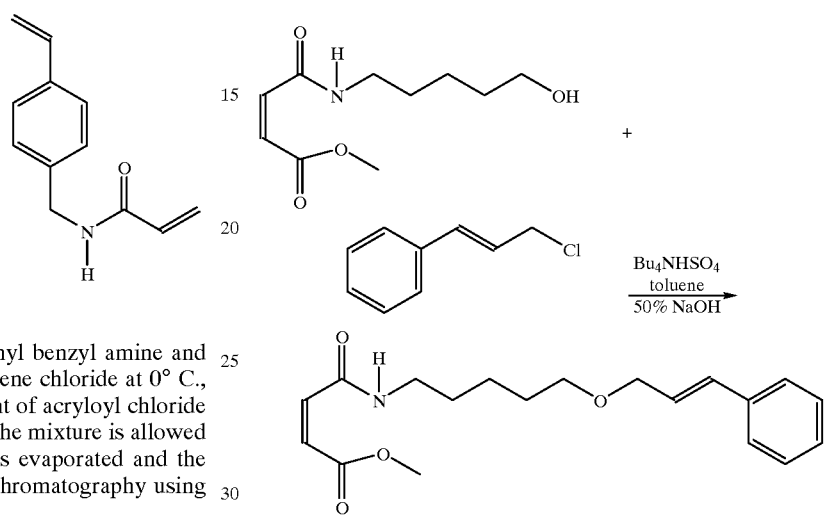

One molar equivalent of hydroxyl amic ester, excess of 50% NaOH, 0.43 molar equivalent of tetrabutyl ammonium hydrogen sulfate, and one molar equivalent of cinnamyl chloride in toluene are stirred for five hours at 53° C., then for 15 hours at 75° C. The reaction is allowed to cool to room temperature and the organic layer extracted and washed with brine three times. The isolated organic layer is dried over MgSO$_4$, filtered and the solvent removed in vacuo to the product.

Example 20

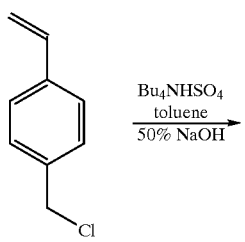

-continued

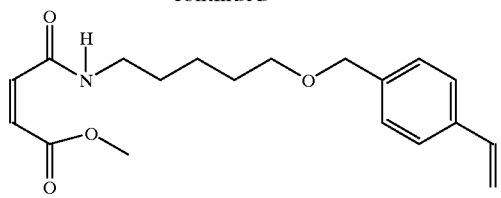

One molar equivalent of hydroxyl amic ester, excess of 50% NaOH, 0.43 molar equivalent of tetrabutyl ammonium hydrogen sulfate, and one molar equivalent of 4-vinyl benzyl chloride in toluene are stirred for five hours at 53° C., then for 15 hours at 75° C. The reaction is allowed to cool to room temperature and the organic layer extracted and washed with brine three times. The isolated organic layer is dried over MgSO₄, filtered and the solvent removed in vacuo to give the product.

Example 21

Other electron donor/acceptor compounds can be made according to similar procedures. The following reaction schemes show other starting electron-donor compounds and starting electron-acceptor compounds with the resulting electron donor/acceptor compounds.

Example 21-A

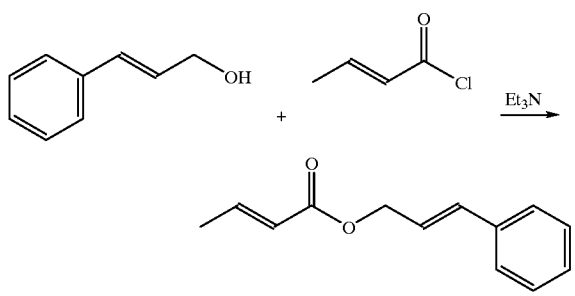

Example 21-B

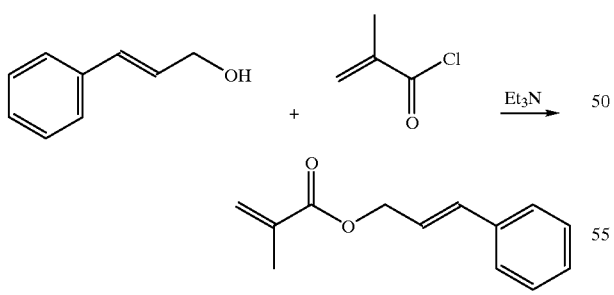

Example 21-C

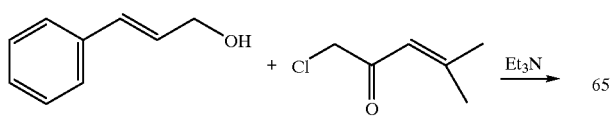

-continued

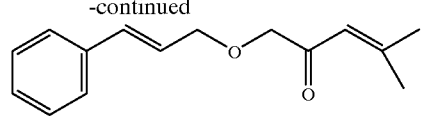

Example 21-D

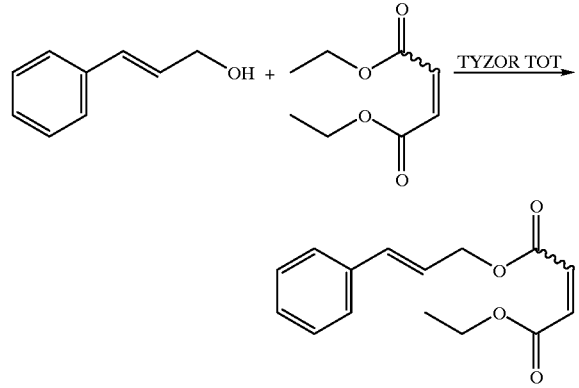

TYZOR TOT is a titanium catalyst available from Aldrich.

Example 21-E

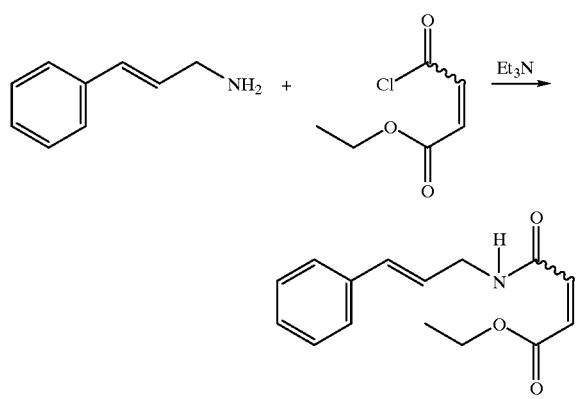

Example 21-F

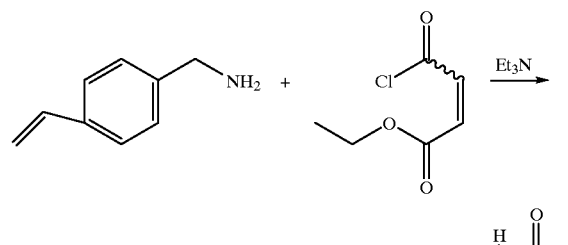

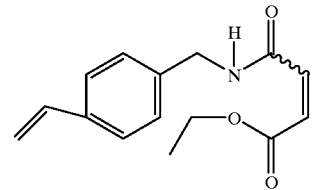

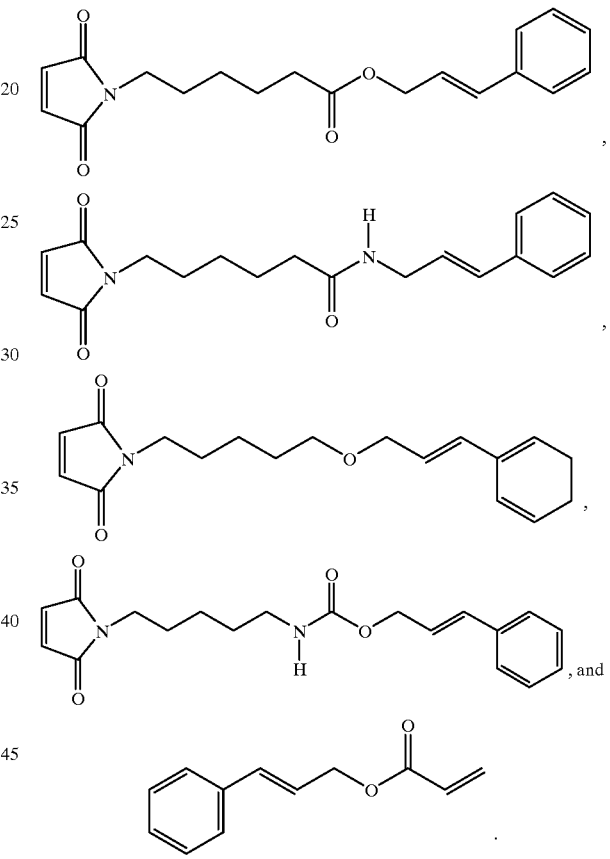

What is claimed is:

1. A compound having the structure

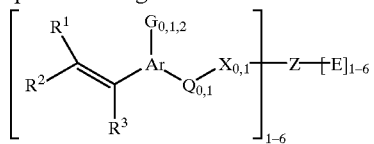

in which

Ar is an aromatic or heteroaromatic ring or fused ring having 3 to 10 carbon atoms within the ring structure, in which the heteroatom is N, O or S;

$R^1$, $R^2$ and $R^3$ are independently hydrogen, a branched, cyclic or linear alkyl group having 1 to 12 carbon atoms, or Ar as described above;

G is $-OR^4$, $-SR^4$, $-N(R^1)(R^2)$, Ar as described above, or an alkyl group having 1 to 12 carbon atoms, in which $R^1$ and $R^2$ are as described above, and $R^4$ is Ar as described above or an alkyl group having 1 to 12 carbon atoms;

Q is an alkyl group having 1 to 12 carbon atoms;

X is:

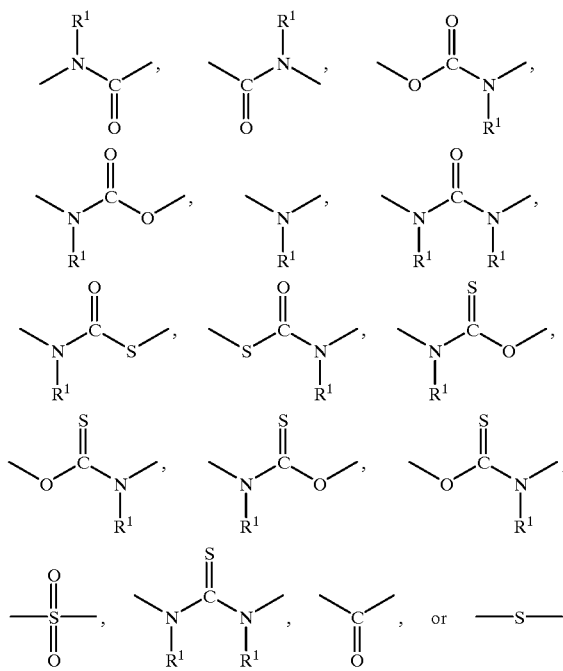

Z is an alkyl group, a siloxane, a polysiloxane, a $C_1$ to $C_4$ alkoxy-terminated siloxane or polysiloxane, a polyether, a polyester, a polyurethane, a poly(butadiene) or an aromatic, polyaromatic, or heteroaromatic group; and E is

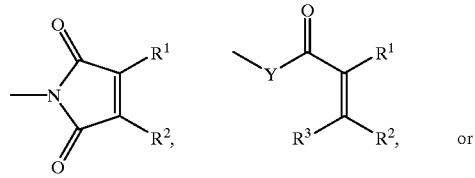

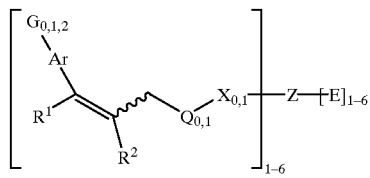

in which Y is O or $N(R^1)$ and $R^1$, $R^2$, and $R^3$ and Q are as described above.

2. A compound according to claim 1 selected from the group of compounds:

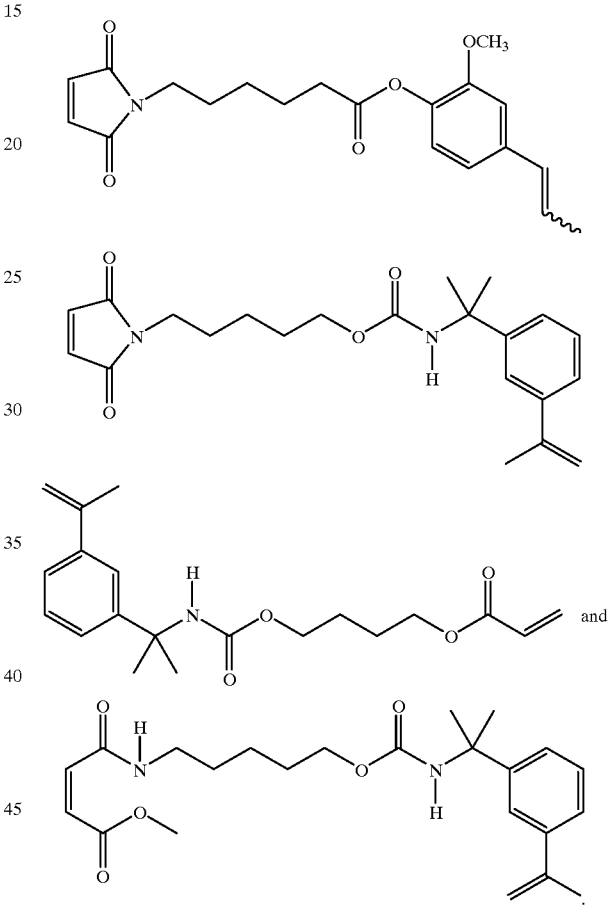

3. A compound having the structure in which

Ar is an aromatic or heteroaromatic ring or fused ring having 3 to 10 carbon atoms within the ring structure, in which the heteroatom is N, O or S;

$R^1$, $R^2$ and $R^3$ are independently hydrogen, a branched, cyclic or linear alkyl group having 1 to 12 carbon atoms, or Ar as described above;

G is —OR⁴, —SR⁴, —N(R¹)(R²), Ar as described above, or an alkyl group having 1 to 12 carbon atoms, in which R¹ and R² are as described above, and R⁴ is Ar as described above or an alkyl group having 1 to 12 carbon atoms;

Q is an alkyl group having 1 to 12 carbon atoms;

X is:

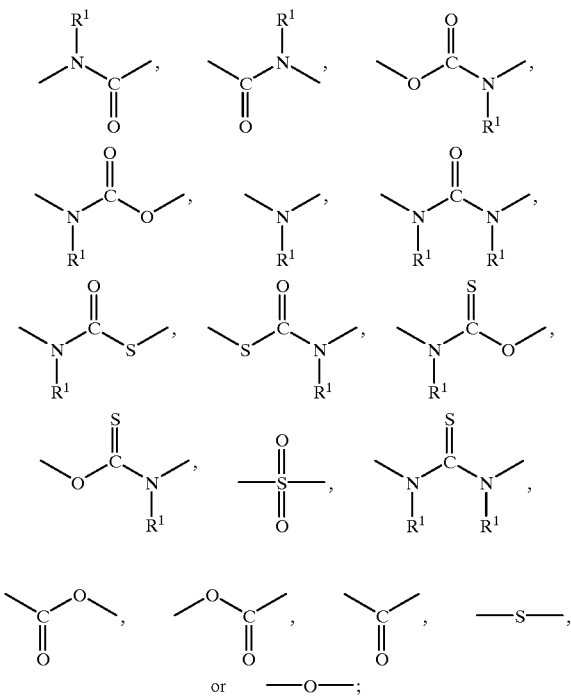

Z is an alkyl group, a siloxane, a polysiloxane, a $C_1$ to $C_4$ alkoxy-terminated siloxane or polysiloxane, a polyether, a polyester, a polyurethane, a poly(butadiene) or an aromatic, polyaromatic, or heteroaromatic group; and E is

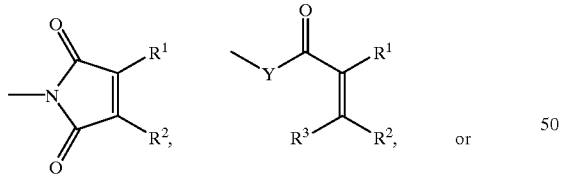 or

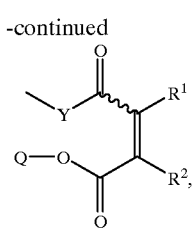

in which Y is O or N(R¹) and R¹, R², and R³ and Q are as described above.

4. A compound according to claim 3 selected from the group of compounds: